(12) United States Patent
Goeddel et al.

(10) Patent No.: US 6,838,550 B2
(45) Date of Patent: Jan. 4, 2005

(54) SUPPRESSORS OF DEATH DOMAINS

(75) Inventors: David V. Goeddel, Hillsborough, CA (US); Yingping Jiang, South San Francisco, CA (US)

(73) Assignee: Arngen Inc., South San Francisco, CA (US)

( * ) Notice: Subject to any disclaimer, the term of this patent is extended or adjusted under 35 U.S.C. 154(b) by 393 days.

(21) Appl. No.: 10/161,346

(22) Filed: May 30, 2002

(65) Prior Publication Data

US 2003/0166193 A1 Sep. 4, 2003

Related U.S. Application Data

(63) Continuation of application No. 09/035,676, filed on Mar. 5, 1998, now Pat. No. 6,437,113.

(51) Int. Cl.[7] .......................... C07K 1/100; G01N 33/48
(52) U.S. Cl. ........................................ 530/350; 436/64
(58) Field of Search ............................. 530/350; 436/64

(56) References Cited

U.S. PATENT DOCUMENTS

| | | |
|---|---|---|
| 4,889,806 A | 12/1989 | Olson et al. |
| 5,168,048 A | 12/1992 | Quax |

OTHER PUBLICATIONS

Schiffmann, S. et al. Isolation of cDNA clones encoding adenosine-5'-phosphosulfate-kinase (EC 2.7.1.25) and an Isoform (akn2) from Arabidopsis (Accession No. AF043351). Plant Physiology. Jan. 1998, vol. 117, No. 3, p. 1125, esp p. 1125.

Arz, H.E. et al. A cDNA for Adenyl Sulphate (APS) -kinase from Arabidopsis thaliana: Biochimica et Biophysica Acta. 1994, vol. 1218, No. 3, pp. 447–452 esp p. 449.
Ahn et al., Nature Genes, 1993, 3:283–91.
Harris et al., J. Am. Soc. Nephrol., 1995, 6:1125–33.
Cawthon et al., Genomics, 1991, 9:446–60.
Marra et al. Genbank Accession No. AA681281 Dec. 5, 1997.
Hum et al. Virology. vol. 170 p. 55–61 1989.
Marra et al. Genbank Accession No. AA184680 Jan. 12, 1997.
Hillier et al. Genbank Accession No. H53288 Sep. 20, 1995.
Hillier et al. Genbank Accession No. H79217 Nov. 9, 1995.
Hillier et al. Genbank Accession No. AA002044 Dec. 5, 1997.
Kitt, Genbank Accession No. CVU13188 Mar. 29, 1996.
Adams et al. Accession No. AA304656 1995.
Hillier et al., Genbank Accession No. AA002044 May 7, 1997.
Marra et al. Genbank Accession No. AA537374 Jul. 29, 1997.

*Primary Examiner*—Gary B. Nickol
(74) *Attorney, Agent, or Firm*—Richard Aron Osman

(57) ABSTRACT

The invention provides methods and compositions relating to Suppressor of Death Domain (SODD) proteins which regulate cellular signal transduction and transcriptional activation, and related nucleic acids. The polypeptides may be produced recombinantly from transformed host cells from the disclosed SODD encoding nucleic acids or purified from human cells. The invention provides isolated SODD hybridization probes and primers capable of specifically hybridizing with the disclosed SODD genes, SODD-specific binding agents such as specific antibodies, and methods of making and using the subject compositions in diagnosis, therapy and in the biopharmaceutical industry.

4 Claims, No Drawings

SUPPRESSORS OF DEATH DOMAINS

CROSS-REFERENCE TO RELATED APPLICATION

This application is a continuation of U.S. Ser. No. 09/035,676, filed Mar. 5, 1998, now U.S. Pat. No. 6,437,113 which is incorporated herein by reference.

INTRODUCTION

1. Field of the Invention

The field of this invention is proteins involved in cell signal transduction.

2. Background

Tumor necrosis factor (TNF) is an important cytokine involved in the signaling of a number of cellular responses including cytotoxicity, anti-viral activity, immun-regulatory activities and the transcriptional regulation of a number of genes. The TNF receptors (TNFR1 and TNFR2) are members of the larger TNF receptor superfamily which also includes the Fas antigen, CD27, CD30, CD40, and several other receptors (Smith et al., 1996, Cell 75, 959–962). Members of this family have been shown to participate in a variety of biological properties, including programmed cell death, antiviral activity and activation of the transcription factor NF-κB in a wide variety of cell types. In particular, death domain containing members of this family, such as TNFR1 and Fas, can induce programmed cell death through a shared ~80 amino acid death domain (Tartaglia et al., 1993, Cell 74, 845–853; Itoh et al., 1993, J. Biol.Chem. 258, 10932–10937).

Additional intracellular death domain containing proteins are identified through yeast two-hybrid interaction cloning by virtue of their interactions with the death domains of death domain containing members of the TNF receptor superfamily. For example, TRADD has been shown to interact specifically with TNFR1 (Hsu, et al., 1995, Cell 81, 495–504) and FADD (Boldin et al., 1995, J. Biol.Chem. 270, 7795–7798; Chinnaiyan et al., 1995, Cell 81, 505–512) and RIP (Stanger et al., 1995, Cell 81, 513–523) interact specifically with Fas. In fact, death domains define interaction domains that provide both homotypic and heterotypic associations and can function as adapters to couple members of the TNFR superfamily with other signaling proteins (see, e.g. Hsu et al. (1996) Cell 84, 299–308).

Accordingly, the ability to exogenously modulate the activity of death domain containing proteins would yield therapeutic application for numerous clinical indications. In addition, components of such pathways would provide valuable target reagents for automated, cost-effective, high throughput drug screening assays and hence would have immediate application in domestic and international pharmaceutical and biotechnology drug development programs. The present invention provides novel modulators of death domains, their use, e.g. in drug screens, modulating cellular function, etc.

SUMMARY OF THE INVENTION

The invention provides methods and compositions relating to isolated Suppressor of Death Domain (SODD) polypeptides, related nucleic acids, polypeptide domains thereof having SODD-specific structure and activity and modulators of SODD function, particularly death domain binding activity. SODD polypeptides can regulate death domain containing proteins, including members of the TNFR superfamily and hence provide important regulators of cell function such as NFκB activation. The polypeptides may be produced recombinantly from transformed host cells from the subject SODD polypeptide encoding nucleic acids or purified from mammalian cells. The invention provides isolated SODD gene hybridization probes and primers capable of specifically hybridizing with the disclosed SODD-encoding genes, SODD-specific binding agents such as specific antibodies, and methods of making and using the subject compositions in diagnosis (e.g. nucleic acid hybridization screens for SODD transcripts), modulating cellular physiology (e.g. modulating intracellular SODD activity to modulate TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of a natural cDNA encoding a human SODD polypeptide is shown as SEQ ID NO:1, and the full conceptual translate is shown as SEQ ID NO:2. The SODD polypeptides of the invention include one or more functional domains of SEQ ID NO:2, which domains comprise at least 8, preferably at least 16, more preferably at least 32, most preferably at least 64 contiguous residues of SEQ ID NO:2 including at least one, preferably at least two, more preferably at least 4 and most preferably all of said contiguous residues contained within at least one of residues 1–122, residues 180–237 and residues 450–457, and have human SODD-specific amino acid sequence and activity. SODD domain specific activities include TNFR superfamily death domain-binding and/or binding inhibitory activity and SODD-specific immunogenicity and/or antigenicity.

SODD-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an SODD polypeptide with a binding target is evaluated. The binding target may be a natural intracellular binding target such as an SODD binding target, a SODD regulating protein or other regulator that directly modulates SODD activity or its localization; or non-natural binding target such a specific immune protein such as an antibody, or an SODD specific agent such as those identified in screening assays such as described below. SODD-binding specificity may be assayed by binding equilibrium constants (usually at least about $10^7 M^{-1}$, preferably at least about $10^8 M^{-1}$, more preferably at least about $10^9 M^{-1}$), by NFκB reporter expression, by apoptosis assays, by the ability of the subject polypeptide to function as negative mutants in SODD-expressing cells, to elicit SODD specific antibody in a heterologous host (e.g a rodent or rabbit), etc.

For example, deletion mutagenesis is used to defined functional SODD domains which bind and sequester TNFR superfamily death domains, inhibit apoptosis or inhibit NFκB expression in SODD-modulated NFκB activation assays. See, e.g. Table 1.

TABLE 1

Exemplary SODD deletion mutants defining SODD functional domains.

| Mutant | Sequence | Death Domain Binding | Apoptosis Inhibition | NFκB Inhibition |
|---|---|---|---|---|
| ΔN1 | SEQ ID NO: 2, residues 23–457 | + | + | + |
| ΔN2 | SEQ ID NO: 2, residues 68–457 | + | + | + |
| ΔN3 | SEQ ID NO: 2, residues 118–457 | + | + | + |
| ΔN4 | SEQ ID NO: 2, residues 185–457 | + | + | + |
| ΔN5 | SEQ ID NO: 2, residues 261–457 | + | + | + |
| ΔC1 | SEQ ID NO: 2, residues 1–456 | + | + | + |
| ΔC2 | SEQ ID NO: 2, residues 1–420 | − | − | − |
| ΔC3 | SEQ ID NO: 2, residues 1–373 | − | − | − |
| ΔC4 | SEQ ID NO: 2, residues 1–277 | − | − | − |

In a particular embodiment, the subject domains provide SODD-specific antigens and/or immunogens, especially when coupled to carrier proteins. For example, peptides corresponding to SODD- and human SODD-specific domains are covalently coupled to keyhole limpet antigen (KLH) and the conjugate is emulsified in Freunds complete adjuvant. Laboratory rabbits are immunized according to conventional protocol and bled. The presence of SODD-specific antibodies is assayed by solid phase immunosorbant assays using immobilized SODD polypeptides of SEQ ID NO:2, see, e.g. Table 2.

TABLE 2

Immunogenic SODD polypeptides eliciting SODD-specific rabbit polyclonal antibody: SODD polypeptide-KLH conjugates immunized per protocol described above.

| SODD Polypeptide Sequence | Immunogenicity |
|---|---|
| SEQ ID NO: 2, residues 1–10 | +++ |
| SEQ ID NO: 2, residues 12–21 | +++ |
| SEQ ID NO: 2, residues 25–37 | +++ |
| SEQ ID NO: 2, residues 42–59 | +++ |
| SEQ ID NO: 2, residues 62–71 | +++ |
| SEQ ID NO: 2, residues 72–85 | +++ |
| SEQ ID NO: 2, residues 105–112 | +++ |
| SEQ ID NO: 2, residues 116–122 | +++ |
| SEQ ID NO: 2, residues 120–128 | +++ |
| SEQ ID NO: 2, residues 175–182 | +++ |
| SEQ ID NO: 2, residues 180–195 | +++ |
| SEQ ID NO: 2, residues 201–208 | +++ |
| SEQ ID NO: 2, residues 213–222 | +++ |
| SEQ ID NO: 2, residues 222–230 | +++ |
| SEQ ID NO: 2, residues 228–237 | +++ |
| SEQ ID NO: 2, residues 230–338 | +++ |
| SEQ ID NO: 2, residues 237–245 | +++ |
| SEQ ID NO: 2, residues 440–450 | +++ |
| SEQ ID NO: 2, residues 442–451 | +++ |
| SEQ ID NO: 2, residues 445–452 | +++ |
| SEQ ID NO: 2, residues 447–454 | +++ |
| SEQ ID NO: 2, residues 449–456 | +++ |
| SEQ ID NO: 2, residues 450–457 | +++ |

The claimed SODD polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The SODD polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York) or that are otherwise known in the art.

The invention provides binding agents specific to SODD polypeptides, preferably the claimed SODD polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g TNF signal transduction. Novel SODD-specific binding agents include SODD-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate SODD function, e.g. SODD-modulatable signal transduction.

Accordingly, the invention provides methods for modulating apoptosis and/or death domain function, particularly TNFR superfamily death domain function, more particularly, TNFR1 and/or DR3 death domain function in a cell comprising the step of modulating SODD activity. The cell may reside in culture or in situ, i.e. within the natural host. Generally, agents are introduced into the cell which effect an upregulation in the activity of intracellular SODD polypeptides. For example, SODD-encoding polypeptides may be transfected into the cell under conditions which effect the expression of the encoded SODD polypeptides.

The amino acid sequences of the disclosed SODD polypeptides are used to back-translate SODD polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural SODD-encoding nucleic acid sequences ("GCG" software, Genetics Computer Group, Inc, Madison, Wis. SODD-encoding nucleic acids used in SODD-expression vectors and incorporated into recombinant host cells, e.g. for expression and screening, transgenic animals, e.g. for functional studies such as the efficacy of candidate drugs for disease associated with SODD-modulated cell function, etc.

The invention also provides nucleic acid hybridization probes and replication/amplification primers having a SODD cDNA specific sequence comprising at least 12, preferably at least 24, more preferably at least 36 and most preferably at least 96 contiguous bases of a strand of SEQ ID NO:1 including at least two contiguous nucleotides contained within at least one of nucleotides 1–366, nucleotides 537–711 and residues 1348–1444 and preferably sufficient to specifically hybridize with a second nucleic acid comprising the complementary strand of SEQ ID NO:1. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

TABLE 3

Exemplary SODD nucleic acids which hybridize with a strand of SEQ ID NO: 1 under Conditions I and/or II.

| SODD Nucleic Acids | Hybridization |
|---|---|
| SEQ ID NO: 1, nucleotides 1–36 | + |
| SEQ ID NO: 1, nucleotides 68–98 | + |
| SEQ ID NO: 1, nucleotides 95–130 | + |
| SEQ ID NO: 1, nucleotides 175–220 | + |
| SEQ ID NO: 1, nucleotides 261–299 | + |
| SEQ ID NO: 1, nucleotides 274–310 | + |
| SEQ ID NO: 1, nucleotides 331–369 | + |
| SEQ ID NO: 1, nucleotides 530–570 | + |
| SEQ ID NO: 1, nucleotides 584–616 | + |
| SEQ ID NO: 1, nucleotides 661–708 | + |
| SEQ ID NO: 1, nucleotides 689–725 | + |
| SEQ ID NO: 1, nucleotides 1328–1365 | + |
| SEQ ID NO: 1, nucleotides 1338–1358 | + |
| SEQ ID NO: 1, nucleotides 1348–1372 | + |
| SEQ ID NO: 1, nucleotides 1365–1399 | + |
| SEQ ID NO: 1, nucleotides 1402–1423 | + |
| SEQ ID NO: 1, nucleotides 1417–1444 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of SODD genes and gene transcripts and in detecting or amplifying nucleic acids encoding additional SODD homologs and structural analogs. In diagnosis, SODD hybridization probes find use in identifying wild-type and mutant SODD alleles in clinical and laboratory samples. Mutant alleles are used to generate allele-specific oligonucleotide (ASO) probes for high-throughput clinical diagnoses. In therapy, therapeutic SODD nucleic acids are used to modulate cellular expression or intracellular concentration or availability of active SODD.

The invention provides efficient methods of identifying agents, compounds or lead compounds for agents active at the level of a SODD modulatable cellular function. Generally, these screening methods involve assaying for compounds which modulate SODD interaction with a natural SODD binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an SODD polypeptide, which may be part of a fusion product with another peptide or polypeptide, e.g. a tag for detection or anchoring, etc. The assay mixtures comprise a natural intracellular SODD binding target. While native full-length binding targets may be used, it is frequently preferred to use portions (e.g. peptides) thereof so long as the portion provides binding affinity and avidity to the subject SODD polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the SODD polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the SODD polypeptide and one or more binding targets is detected by any convenient way. A difference in the binding affinity of the SODD polypeptide to the target in the absence of the agent as compared with the binding affinity in the presence of the agent indicates that the agent modulates the binding of the SODD polypeptide to the SODD binding target. Analogously, in the cell-based assay also described below, a difference in SODD-dependent transcriptional activation in the presence and absence of an agent indicates the agent modulates SODD function. A difference, as used herein, is statistically significant and preferably represents at least a 50%, more preferably at least a 90% difference.

The following experimental section and examples are offered by way of illustration and not by way of limitation.

EXAMPLES

1. Experimental Procedures

Recombinant human TNF and MAb 985 against the extracellular domain of TNFR1 were obtained from Genentech, Inc.; anti-Flag MAb M2 from Eastman Kodak Company; and anti-Flag polyclonal antibodies from Santa Cruz Biotechnology. SODD polypeptide specific polyclonal antisera were generated against a SODD peptide (residues 292 to 313) and against His-tagged native SODD protein. Human embryonic kidney 293 cells, HeLa cells, U937 cells and Jurkat cells were maintained as described by Hsu et al. (1996) Cell 84, 299–308.

A native human SODD protein was originally identified as a DR3-interacting protein by two hybrid screening. The plasmid Gal4BD-DR3, which encodes the GAL4 DNA-binding domain fused to the intracellular domain of DR3, was used as bait in two-hybrid screens of a HeLa cell cDNA library (Clontech). The isolated positive clones were analyzed as described by Hsu et al. (supra). Full length SODD cDNA was obtained by screening a human Jurkat T cell cDNA library in lZAP by standard methods (Sambrook et al., 1989).

For northern analysis, the native SODD cDNA was used to probed a human multiple tissue Northern blot (Clontech), according to the manufacturer's protocol. These assays revealed broad tissue distribution of SODD transcripts, including immune cells.

Mammalian cell expression vectors encoding TNFR1, TRADD, crmA and control plasmid pRK5 have been described previously Hsu et al. (supra). An expression vector for N-terminally Flag-tagged SODD polypeptide was constructed in the expression vector in pRK. Deletion mutants of native SODD protein were generated by inserting PCR fragments encoding corresponding SODD amino acid sequences in-frame with an N-terminal Flag epitope coding sequence in the vector pRK.

For coimmunoprecipitation assays, subconfluent 10 cm dish cultures of 293 cells were transfected by the calcium phosphate method. 24 hours after transfection, cells were washed in PBS and lysed in EIA lysis buffer {Hsu}. Lysates were incubated for 2–4 hours at 4° C. with anti-TNFR1 monoclonal antibody (985) or control mouse IgG monoclonal antibody (Sigma) and 25 ml of 1:1 slurry of protein G-Sepharose (Pharmacia). Beads were washed twice with 1 ml E1A buffer, twice with 1 ml of high salt (1 M NaCl) E1A buffer, and twice again with E1A buffer. The precipitates were fractionated on SDS-PAGE and transferred to nitrocellulose membrane. Western blotting analyzes were performed using standard procedures.

For endogenous association assay, U937 cells ($2 \times 10^8$) and Jurkat cells ($5 \times 10^7$) were washed with warm PBS, and incubated at 15 min in the presence or absence of TNF (100 ng/ml). Cells were lysed in Triton-X-100 lysis buffer and resultant lysates incubated with 25 mg of MAb 985 or mouse IgG and protein G-Sepharose (Pharmacia) at 4° C. overnight. The beads were washed twice with lysis buffer, twice with 1 ml high salt lysis buffer, and again with lysis buffer. The samples were separated on SDS-PAGE, and analyzed as above.

2. Protocol for Cell-Based NF-κB Reporter Assay

SODD can inhibit transactivation of NF-kB reporter constructs when overexpressed in 293 cells or HeLa cells. 293 cells are transfected using the calcium phosphate precipitation method with a plasmid encoding a 6 NF-kB-luciferase reporter construct and various amounts of expression vector encoding SODD. After 36–48 hours, cells are left untreated or treated with IL-1 (10–50 ng/ml) or TNF (50–100 ng) for 6 hours prior to harvest. Cells are lysed and luciferase activity measured using the luciferase assay kit (Promega). The luciferase activity in each transfection is normalized by co-transfecting a pRSV-β gal control vector.

3. Protocol for high throughput in vitro SODD-TNFR1 Death Domain binding assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P SODD polypeptide 10× stock: $10^{-8}$–$10^{-6}$M "cold" SODD supplemented with 200,000–250,000 cpm of labeled SODD (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVO$_3$ (Sigma # S-6508) in 10 ml of PBS.

TNFR1 deletion mutant: $10^{-7}$–$10^{-5}$M biotinylated TNFR1 80 residue death domain in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-SODD (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 μM biotinylated TNFR1 deletion mutant (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all assays (located on each plate):

a. Non-specific binding b. Soluble (non-biotinylated TNFR1 deletion mutant) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purpose of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising a human SODD (SEQ ID NO:2) or functional domain thereof sufficient to bind and sequester TNFR superfamily death domains, inhibit apoptosis, or inhibit NFκB expression in SODD-modulated NFκB activation assays.

2. An isolated polypeptide according to claim 1, wherein the functional domain comprises a sequence selected from the group consisting of residues 23-457, 68-457, 118-457, 185-457, 261-457 and 1-456 of SEQ ID NO:2.

3. An isolated polypeptide according to claim 1, wherein the polypeptide comprises a human SODD (SEQ ID NO:2).

4. An isolated polypeptide according to claim 1, wherein the polypeptide consists of a human SODD (SEQ ID NO:2).

* * * * *

UNITED STATES PATENT AND TRADEMARK OFFICE
CERTIFICATE OF CORRECTION

| | | |
|---|---|---|
| PATENT NO. | : 6,838,550 B2 | Page 1 of 1 |
| APPLICATION NO. | : 10/161346 | |
| DATED | : January 4, 2005 | |
| INVENTOR(S) | : Goeddel et al. | |

It is certified that error appears in the above-identified patent and that said Letters Patent is hereby corrected as shown below:

On Title Page, Item (73), the Assignee should read --Amgen Inc., Thousand Oaks, CA--

Signed and Sealed this

Sixth Day of March, 2007

JON W. DUDAS
*Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1444 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1371

(xi) SEQUENCE DESCRIPTION: SEQ ID NO: 1:

```
ATG TCG GCC CTG AGG CGC TCG GGC TAC GGC CCC AGT GAC GGT CCG TCC       48
Met Ser Ala Leu Arg Arg Ser Gly Tyr Gly Pro Ser Asp Gly Pro Ser
 1               5                  10                  15

TAC GGC CGC TAC TAC GGG CCT GGG GGT GGA GAT GTG CCG GTA CAC CCA       96
Tyr Gly Arg Tyr Tyr Gly Pro Gly Gly Gly Asp Val Pro Val His Pro
                20                  25                  30

CCT CCA CCC TTA TAT CCT CTT CGC CCT GAA CCT CCC CAG CCT CCC ATT      144
Pro Pro Pro Leu Tyr Pro Leu Arg Pro Glu Pro Pro Gln Pro Pro Ile
            35                  40                  45

TCC TGG CGG GTG CGC GGG GGC GGC CCG GCG GAG ACC ACC TGG CTG GGA      192
Ser Trp Arg Val Arg Gly Gly Gly Pro Ala Glu Thr Thr Trp Leu Gly
         50                  55                  60

GAA GGC GGA GGA GGC GAT GGC TAC TAT CCC TCG GGA GGC GCC TGG CCA      240
Glu Gly Gly Gly Gly Asp Gly Tyr Tyr Pro Ser Gly Gly Ala Trp Pro
 65                  70                  75                  80

GAG CCT GGT CGA GCC GGA GGA AGC CAC CAG GAG CAG CCA CCA TAT CCT      288
Glu Pro Gly Arg Ala Gly Gly Ser His Gln Glu Gln Pro Pro Tyr Pro
                85                  90                  95

AGC TAC AAT TCT AAC TAT TGG AAT TCT ACT GCG AGA TCT AGG GCT CCT      336
Ser Tyr Asn Ser Asn Tyr Trp Asn Ser Thr Ala Arg Ser Arg Ala Pro
                100                 105                 110

TAC CCA AGT ACA TAT CCT GTA AGA CCA GAA TTG CAA GGC CAG AGT TTG      384
Tyr Pro Ser Thr Tyr Pro Val Arg Pro Glu Leu Gln Gly Gln Ser Leu
            115                 120                 125

AAT TCT TAT ACA AAT GGA GCG TAT GGT CCA ACA TAC CCC CCA GGC CCT      432
Asn Ser Tyr Thr Asn Gly Ala Tyr Gly Pro Thr Tyr Pro Pro Gly Pro
        130                 135                 140

GGG GCA AAT ACT GCC TCA TAC TCA GGG GCT TAT TAT GCA CCT GGT TAT      480
Gly Ala Asn Thr Ala Ser Tyr Ser Gly Ala Tyr Tyr Ala Pro Gly Tyr
145                 150                 155                 160

ACT CAG ACC AGT TAC TCC ACA GAA GTT CCA AGT ACT TAC CGT TCA TCT      528
Thr Gln Thr Ser Tyr Ser Thr Glu Val Pro Ser Thr Tyr Arg Ser Ser
                165                 170                 175

GGC AAC AGC CCA ACT CCA GTC TCT CGT TGG ATC TAT CCC CAG CAG GAC      576
Gly Asn Ser Pro Thr Pro Val Ser Arg Trp Ile Tyr Pro Gln Gln Asp
                180                 185                 190

TGT CAG ACT GAA GCA CCC CCT CTT AGG GGG CAG GTT CCA GGA TAT CCG      624
Cys Gln Thr Glu Ala Pro Pro Leu Arg Gly Gln Val Pro Gly Tyr Pro
            195                 200                 205

CCT TCA CAG AAC CCT GGA ATG ACC CTG CCC CAT TAT CCT TAT GGA GAT      672
Pro Ser Gln Asn Pro Gly Met Thr Leu Pro His Tyr Pro Tyr Gly Asp
        210                 215                 220
```

-continued

```
GGT AAT CGT AGT GTT CCA CAA TCA GGA CCG ACT GTA CGA CCA CAA GAA      720
Gly Asn Arg Ser Val Pro Gln Ser Gly Pro Thr Val Arg Pro Gln Glu
225                 230                 235                 240

GAT GCG TGG GCT TCT CCT GGT GCT TAT GGA ATG GGT GGC CGT TAT CCC      768
Asp Ala Trp Ala Ser Pro Gly Ala Tyr Gly Met Gly Gly Arg Tyr Pro
                245                 250                 255

TGG CCT TCA TCA GCG CCC TCA GCA CCA CCC GGC AAT CTC TAC ATG ACT      816
Trp Pro Ser Ser Ala Pro Ser Ala Pro Pro Gly Asn Leu Tyr Met Thr
                260                 265                 270

GAA AGT ACT TCA CCA TGG CCT AGC AGT GGC TCT CCC CAG TCA CCC CCT      864
Glu Ser Thr Ser Pro Trp Pro Ser Ser Gly Ser Pro Gln Ser Pro Pro
            275                 280                 285

TCA CCC CCA GTC CAG CAG CCC AAG GAT TCT TCA TAC CCC TAT AGC CAA      912
Ser Pro Pro Val Gln Gln Pro Lys Asp Ser Ser Tyr Pro Tyr Ser Gln
290                 295                 300

TCA GAT CAA AGC ATG AAC CGG CAC AAC TTT CCT TGC AGT GTC CAT CAG      960
Ser Asp Gln Ser Met Asn Arg His Asn Phe Pro Cys Ser Val His Gln
305                 310                 315                 320

TAC GAA TCC TCG GGG ACA GTG AAC AAT GAT GAT TCA GAT CTT TTG GAT     1008
Tyr Glu Ser Ser Gly Thr Val Asn Asn Asp Asp Ser Asp Leu Leu Asp
                325                 330                 335

TCC CAA GTC CAG TAT AGT GCT GAG CCT CAG CTG TAT GGT AAT GCC ACC     1056
Ser Gln Val Gln Tyr Ser Ala Glu Pro Gln Leu Tyr Gly Asn Ala Thr
                340                 345                 350

AGT GAC CAT CCC AAC AAT CAA GAT CAA AGT AGC AGT CTT CCT GAA GAA     1104
Ser Asp His Pro Asn Asn Gln Asp Gln Ser Ser Ser Leu Pro Glu Glu
                355                 360                 365

TGT GTA CCT TCA GAT GAA AGT ACT CCT CCG AGT ATT AAA AAA ATC ATA     1152
Cys Val Pro Ser Asp Glu Ser Thr Pro Pro Ser Ile Lys Lys Ile Ile
370                 375                 380

CAT GTG CTG GAG AAG GTC CAG TAT CTT GAA CAA GAA GTA GAA GAA TTT     1200
His Val Leu Glu Lys Val Gln Tyr Leu Glu Gln Glu Val Glu Glu Phe
385                 390                 395                 400

GTA GGA AAA AAG ACA GAC AAA GCA TAC TGG CTT CTG GAA GAA ATG CTA     1248
Val Gly Lys Lys Thr Asp Lys Ala Tyr Trp Leu Leu Glu Glu Met Leu
                405                 410                 415

ACC AAG GAA CTT TTG GAA CTG GAT TCA GTT GAA ACT GGG GGC CAG GAC     1296
Thr Lys Glu Leu Leu Glu Leu Asp Ser Val Glu Thr Gly Gly Gln Asp
                420                 425                 430

TCT GTA CGG CAG GCC AGA AAA GAG GCT GTT TGT AAG ATT CAG GCC ATA     1344
Ser Val Arg Gln Ala Arg Lys Glu Ala Val Cys Lys Ile Gln Ala Ile
                435                 440                 445

CTG GAA AAA TTA GAA AAA AAA GGA TTA TGAAAGGATT TAGAACAAAG           1391
Leu Glu Lys Leu Glu Lys Lys Gly Leu
450                 455

GTCGACGCGG CCGCGAATTC CAGATCTATG AATCGTAGAT ACTGAAAAAC CCC          1444
```

(2) INFORMATION FOR SEQ ID NO: 2:

(i) SEQUENCE CHARACTERISTICS:
        (A) LENGTH: 457 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Ala Leu Arg Arg Ser Gly Tyr Gly Pro Ser Asp Gly Pro Ser
1               5                   10                  15

Tyr Gly Arg Tyr Tyr Gly Pro Gly Gly Gly Asp Val Pro Val His Pro
```

-continued

```
                20                  25                  30
Pro Pro Pro Leu Tyr Pro Leu Arg Pro Glu Pro Gln Pro Pro Ile
            35                  40                  45

Ser Trp Arg Val Arg Gly Gly Pro Ala Glu Thr Thr Trp Leu Gly
 50                  55                  60

Glu Gly Gly Gly Asp Gly Tyr Tyr Pro Ser Gly Ala Trp Pro
 65                  70                  75                  80

Glu Pro Gly Arg Ala Gly Gly Ser His Gln Glu Gln Pro Pro Tyr Pro
                85                  90                  95

Ser Tyr Asn Ser Asn Tyr Trp Asn Ser Thr Ala Arg Ser Arg Ala Pro
            100                 105                 110

Tyr Pro Ser Thr Tyr Pro Val Arg Pro Glu Leu Gln Gly Gln Ser Leu
            115                 120                 125

Asn Ser Tyr Thr Asn Gly Ala Tyr Gly Pro Thr Tyr Pro Pro Gly Pro
            130                 135                 140

Gly Ala Asn Thr Ala Ser Tyr Ser Gly Ala Tyr Ala Pro Gly Tyr
145                 150                 155                 160

Thr Gln Thr Ser Tyr Ser Thr Glu Val Pro Ser Thr Tyr Arg Ser Ser
                165                 170                 175

Gly Asn Ser Pro Thr Pro Val Ser Arg Trp Ile Tyr Pro Gln Gln Asp
            180                 185                 190

Cys Gln Thr Glu Ala Pro Pro Leu Arg Gly Gln Val Pro Gly Tyr Pro
            195                 200                 205

Pro Ser Gln Asn Pro Gly Met Thr Leu Pro His Tyr Pro Tyr Gly Asp
            210                 215                 220

Gly Asn Arg Ser Val Pro Gln Ser Gly Pro Thr Val Arg Pro Gln Glu
225                 230                 235                 240

Asp Ala Trp Ala Ser Pro Gly Ala Tyr Gly Met Gly Gly Arg Tyr Pro
                245                 250                 255

Trp Pro Ser Ser Ala Pro Ser Ala Pro Pro Gly Asn Leu Tyr Met Thr
            260                 265                 270

Glu Ser Thr Ser Pro Trp Pro Ser Ser Gly Ser Pro Gln Ser Pro Pro
            275                 280                 285

Ser Pro Pro Val Gln Gln Pro Lys Asp Ser Ser Tyr Pro Tyr Ser Gln
            290                 295                 300

Ser Asp Gln Ser Met Asn Arg His Asn Phe Pro Cys Ser Val His Gln
305                 310                 315                 320

Tyr Glu Ser Ser Gly Thr Val Asn Asn Asp Asp Ser Asp Leu Leu Asp
                325                 330                 335

Ser Gln Val Gln Tyr Ser Ala Glu Pro Gln Leu Tyr Gly Asn Ala Thr
            340                 345                 350

Ser Asp His Pro Asn Asn Gln Asp Gln Ser Ser Ser Leu Pro Glu Glu
            355                 360                 365

Cys Val Pro Ser Asp Glu Ser Thr Pro Pro Ser Ile Lys Lys Ile Ile
            370                 375                 380

His Val Leu Glu Lys Val Gln Tyr Leu Glu Gln Glu Val Glu Glu Phe
385                 390                 395                 400

Val Gly Lys Lys Thr Asp Lys Ala Tyr Trp Leu Leu Glu Glu Met Leu
                405                 410                 415

Thr Lys Glu Leu Leu Glu Leu Asp Ser Val Glu Thr Gly Gly Gln Asp
            420                 425                 430
```

-continued

```
Ser Val Arg Gln Ala Arg Lys Glu Ala Val Cys Lys Ile Gln Ala Ile
        435                 440                 445

Leu Glu Lys Leu Glu Lys Lys Gly Leu
    450                 455
```